(12) United States Patent
Grutta et al.

(10) Patent No.: US 12,376,687 B2
(45) Date of Patent: Aug. 5, 2025

(54) MATTRESS WITH SENSORS

(71) Applicant: Purple Innovation, LLC, Lehi, UT (US)

(72) Inventors: James T. Grutta, Draper, UT (US); Brett Pearson, Taylorsville, UT (US); Thomas Bennett, Irvine, CA (US)

(73) Assignee: Purple Innovation, LLC, Lehi, UT (US)

( * ) Notice: Subject to any disclaimer, the term of this patent is extended or adjusted under 35 U.S.C. 154(b) by 280 days.

(21) Appl. No.: 17/963,845

(22) Filed: Oct. 11, 2022

(65) Prior Publication Data
US 2024/0115059 A1 Apr. 11, 2024

Related U.S. Application Data

(60) Provisional application No. 63/253,947, filed on Oct. 8, 2021.

(51) Int. Cl.
*A47C 27/14* (2006.01)
*A47C 31/12* (2006.01)

(52) U.S. Cl.
CPC .......... *A47C 27/144* (2013.01); *A47C 27/142* (2013.01); *A47C 31/123* (2013.01); *A47C 31/12* (2013.01)

(58) Field of Classification Search
CPC ..... A47C 27/144; A47C 27/142; A47C 27/14; A47C 31/123; A47C 31/12; G08B 21/22; G08B 21/02; G08B 21/18
USPC .................................. 5/690; 340/573.1, 540
See application file for complete search history.

(56) References Cited

U.S. PATENT DOCUMENTS

| | | | | |
|---|---|---|---|---|
| 8,419,660 | B1 * | 4/2013 | Shaw ................... | A61B 5/6892 600/595 |
| 9,005,101 | B1 * | 4/2015 | Van Erlach .......... | A47C 31/123 600/9 |
| 9,782,108 | B2 | 10/2017 | Shimizu | |
| 9,877,593 | B2 * | 1/2018 | Van Erlach .............. | A61N 5/06 |
| 10,080,442 | B2 * | 9/2018 | Chen .................... | A61B 5/6892 |
| 10,542,826 | B2 | 1/2020 | Van Erlach | |

(Continued)

FOREIGN PATENT DOCUMENTS

| | | |
|---|---|---|
| CN | 105962896 B | 11/2019 |
| DE | 102009010379 A1 | 10/2009 |

(Continued)

OTHER PUBLICATIONS

USPTO acting as International Searching Authority, "International Search Report and Written Opinion," International Application No. PCT/US2022/046312, Jan. 20, 2023.

*Primary Examiner* — Robert G Santos
(74) *Attorney, Agent, or Firm* — Foley & Lardner LLP

(57) ABSTRACT

A mattress includes one or more sensors. The sensor(s) may be positioned on a sleep surface of the mattress; for example, at locations where an individual's thorax and/or legs would be positioned when the individual assumes a sleeping position on the sleep surface. The sensor(s) may be positioned adjacent to an edge of the mattress, on the sleep surface or on the edge. A processor may be associated with the sensor(s) of the mattress. The processor may process signals received from the sensor(s) to provide information about the mattress, an individual on the mattress, and/or an environment in which the mattress is located.

19 Claims, 1 Drawing Sheet

(56) References Cited

U.S. PATENT DOCUMENTS

| | | | | |
|---|---|---|---|---|
| 2008/0068182 A1* | 3/2008 | Watson | ................ | A61B 5/053 |
| | | | | 600/300 |
| 2016/0007886 A1* | 1/2016 | Shimizu | ............. | G08B 21/0461 |
| | | | | 340/573.1 |
| 2016/0045035 A1* | 2/2016 | Van Erlach | .......... | A61B 5/0036 |
| | | | | 700/279 |
| 2016/0066703 A1* | 3/2016 | Chen | ...................... | A47C 31/00 |
| | | | | 5/613 |
| 2018/0132627 A1* | 5/2018 | Van Erlach | ........... | A61B 5/1114 |
| 2021/0153779 A1 | 5/2021 | Mizobe et al. | | |
| 2022/0322843 A1* | 10/2022 | Harrison | ................ | A47C 27/15 |
| 2024/0115059 A1* | 4/2024 | Grutta | .................. | A47C 27/144 |
| 2024/0138584 A1* | 5/2024 | Bennett | ................ | A61B 5/4561 |
| 2024/0138585 A1* | 5/2024 | Bennett | ................ | A47C 31/123 |
| 2024/0138586 A1* | 5/2024 | Bennett | ................ | A47C 27/083 |
| 2024/0138587 A1* | 5/2024 | Bennett | ................ | A47C 21/042 |
| 2024/0156277 A1* | 5/2024 | Lazakis | ................ | A47C 27/144 |
| 2024/0245881 A1* | 7/2024 | Bennett | ................ | A47C 21/003 |
| 2024/0251965 A1* | 8/2024 | Bennett | ................ | A47C 21/048 |

FOREIGN PATENT DOCUMENTS

| | | | | |
|---|---|---|---|---|
| KR | | 200467271 Y1 | 6/2013 | |
| WO | WO-2023059940 A1 | * | 4/2023 | ........... A47C 27/144 |
| WO | WO-2024167421 A1 | * | 8/2024 | |

* cited by examiner

MATTRESS WITH SENSORS

CROSS-REFERENCE TO RELATED APPLICATION

A claim for priority to the Oct. 8, 2021 filing date of U.S. Provisional Patent Application No. 63/253,947, titled MATTRESS WITH SENSORS ("the '947 Provisional Application"), is hereby made pursuant to 35 U.S.C. § 119(e). The entire disclosure of the '947 Provisional Application is hereby incorporated herein.

TECHNICAL FIELD

This disclosure relates generally to mattresses and, more specifically, to mattresses with sensors that enable the detection of an individual approaching a mattress, placement of an individual on a top, sleep surface of a mattress, the collection of data about the individual on the sleep surface of the mattress, detection of the removal of the individual from the sleep surface of the mattress, and/or the collection of data regarding an environment (e.g., a room, etc.) in which the mattress is located.

SUMMARY

In various aspects and embodiments, a mattress with one or more sensors is disclosed. The sensor(s) may enable the mattress to be used to monitor a variety of data, including an individual approaching the mattress, the presence of an individual on a sleep surface of the mattress, various information about an individual on the sleep surface, and/or information about an environment (e.g., a room, etc.) within which the mattress is located.

A mattress according to this disclosure includes an upper surface, on which an individual may rest and, thus, which may be referred to as a "sleep surface." The sleep surface includes a head portion, an intermediate portion, and a foot portion. The head portion may receive a head, neck, and shoulders of an individual and, optionally, an upper part of the individual's chest, or thorax. The intermediate portion may receive the individual's chest, abdomen, and hips and, optionally, upper parts of the individual's legs. The foot portion may receive the individual's lower legs and feet.

The mattress includes a cushioning element and the sensor(s). The mattress may also include a rail along each side of the cushioning element. In some embodiments, sensors may be positioned adjacent to the sleep surface and/or one or more edges of the mattress. Without limitation, at least one thoracic sensor may be positioned adjacent to the sleep surface of the head portion of the cushioning element or adjacent to the sleep surface of the intermediate portion of the cushioning element, at a location next to the head portion of the cushioning element. At least one leg sensor may be positioned adjacent to the sleep surface in the foot portion of the cushioning element. At least one edge sensor, which may comprise an ambient environment sensor, may be positioned along a side edge of the mattress (e.g., in a side surface or a top surface of a rail along a side of the cushioning element, etc.).

The at least one thoracic sensor may facilitate detection of the presence (or absence) of an individual on the sleep surface of the mattress. In addition, the at least one thoracic sensor may be used to monitor one or more of the individual's movement (e.g., motion, position on the mattress, etc.), respiration, and heart rate. The at least one thoracic sensor may also monitor the temperature of a portion of the individual's body and, optionally, humidity (e.g., relative humidity generated by a portion of the individual's body, as compared with an ambient relative humidity of environment in which the mattress is located, etc.).

The at least one leg sensor may facilitate the detection of the presence (or absence) of an individual on the sleep surface of the mattress. In addition, the at least one leg sensor may be used to monitor the individual's movement (e.g., motion, position, etc.), respiration, and heart rate. The at least one leg sensor may monitor the temperature of the individual's legs and, optionally, humidity (e.g., a relative humidity generated by the individual's legs, as compared with an ambient relative humidity of the environment in which the mattress is located, etc.).

The at least one edge sensor may facilitate the detection of an individual approaching a side edge of the mattress and/or the presence or absence of an individual on the sleep surface of the mattress. In addition, the at least one edge sensor may be used to monitor information about a room within which the mattress is located, such as its temperature and/or humidity.

Each sensor of the mattress may communicate with a processor of the mattress or of a bed of which the mattress is a part. The processor may receive signals from each sensor and process the signals to provide information about the mattress, an individual approaching the mattress or resting on a sleep surface of the mattress, and/or an environment in which the mattress is located.

In another aspect, methods of monitoring a mattress and its use are disclosed. Such a method may include one or more of detecting when an individual approaches or is present on a sleep surface of the mattress, obtaining information about an individual on the sleep surface of the mattress, detecting when an individual is no longer present on the sleep surface of the mattress, and detecting information about an environment (e.g., a room, etc.) within which the mattress is located.

Data obtained from monitoring the mattress, an individual lying on the mattress, and/or an environment in which the mattress is located may be processed in a manner that enables adjustment of the mattress or the environment around the mattress to improve a quality of the individual's sleep. Without limitation, in embodiments where the mattress is an adjustable mattress carried by an adjustable base, an orientation of one or more parts of the mattress may be adjusted in response to the data. In embodiments where ventilation is associated with the mattress, the ventilation may be adjusted (e.g., in response to temperature and/or humidity data, etc.). In embodiments where the mattress or one or more portions thereof are (internally or externally) heated or cooled, a temperature of one or more portions of the mattress may be adjusted (e.g., in response to temperature and/or humidity data, etc.). In some embodiments, the data obtained from monitoring may be used to make adjustments to the environment in which the mattress is located (e.g., its temperature, humidity, light, ambient sound, etc.).

Features and advantages of various aspects of the disclosed subject matter, as well other aspects of the disclosed subject matter, should become apparent to those of ordinary skill in the art through consideration of this disclosure, the accompanying drawings, and the appended claims.

DETAILED DESCRIPTION

Figure 1:
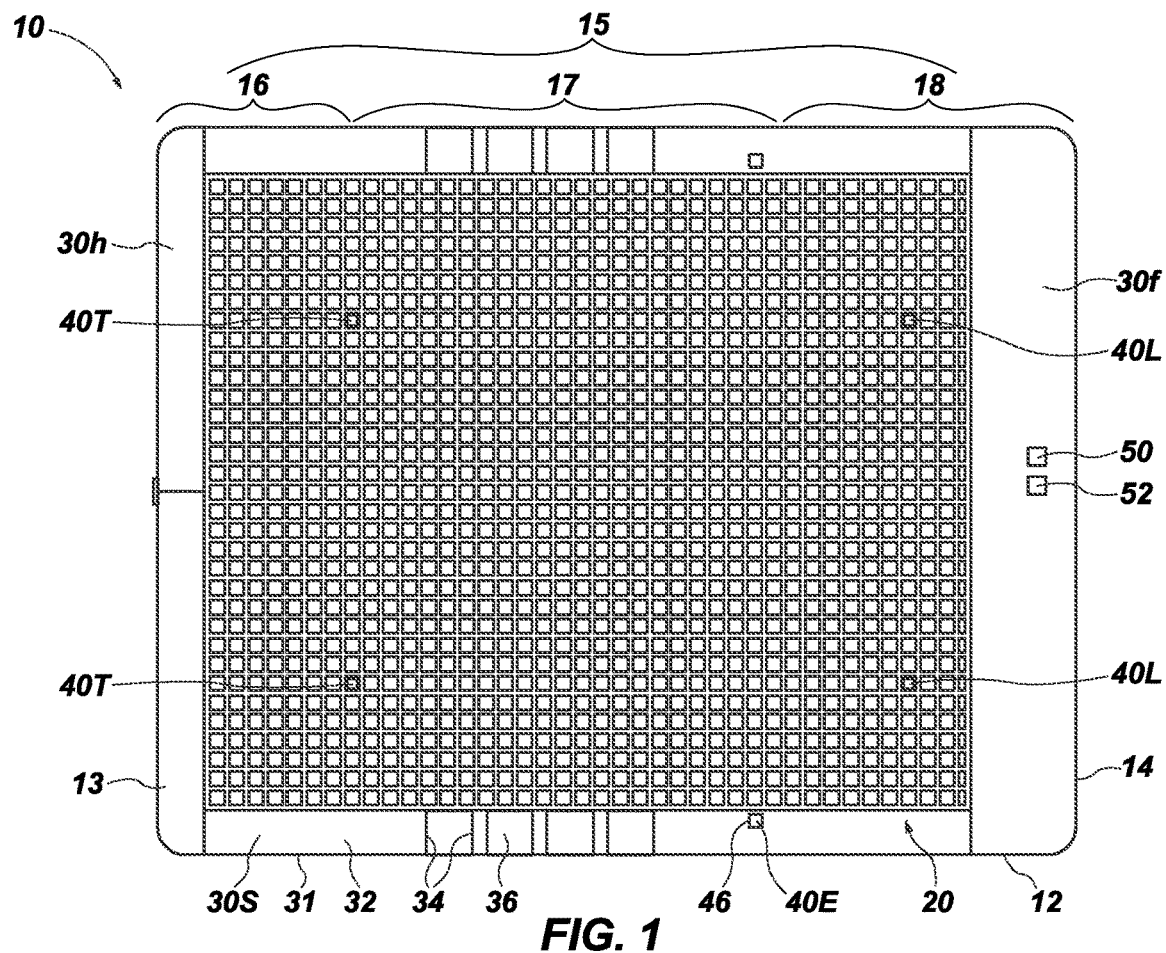
FIG. 1 is a top view of a portion of an embodiment of a mattress with sensors.
Figure 2:
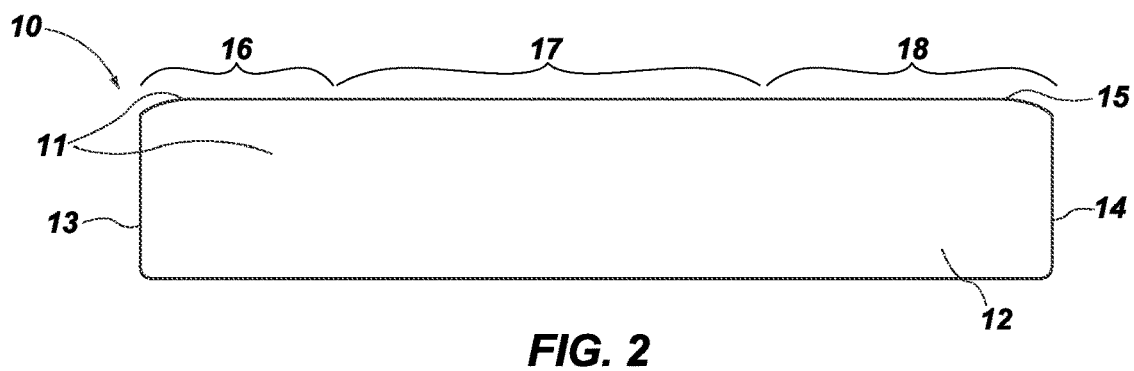
FIG. 2 is a side view of the embodiment of the mattress shown in FIG. 1.
Figure 3:
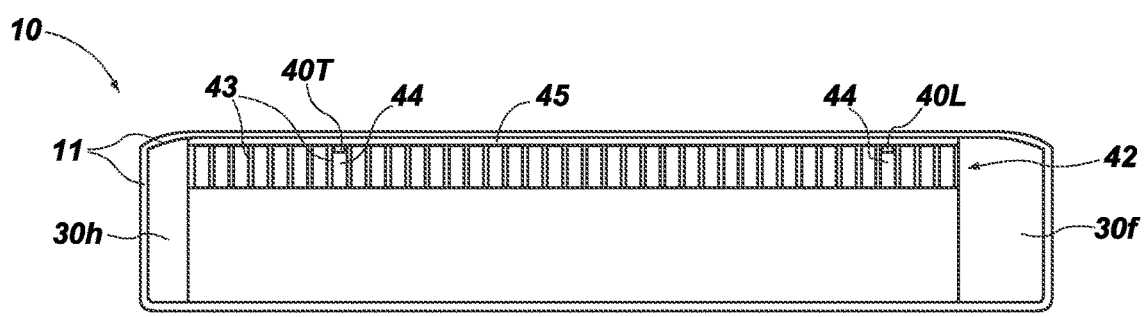
FIG. 3 is a cross-sectional representation of the mattress shown in FIG. 1.

FIGS. 1-3 provide various views of an embodiment of a mattress 10 of this disclosure. The mattress 10 includes a cushioning element 20, rails 30, and one or more sensors 40. The mattress 10 may also include a processor 50. Optionally, the mattress may include a transceiver 52 and associated antenna; the transceiver 52 may communicate with the processor 50. The mattress 10 may also include any of a variety of other optional components.

The mattress 10 may have any suitable shape and dimensions and may include a cover 11 (FIGS. 2 and 3) that contains various internal elements of the mattress 10. Around its periphery, the mattress 10 may include sides 12, a head end 13, and a foot end 14; the head end 13 and foot end 14 may also be referred to as "ends" 13 and 14. The head end 13 may extend between top ends of the sides 12, while the foot end 14 may extend between bottom ends of the sides 12.

An upper surface of the cover 11, which may be referred to as a "sleep surface 15" of the mattress 10, extends between upper edges of the sides 12, the head end 13, and the foot end 14 of the mattress. A configuration of the sleep surface 15 may accommodate at least one individual in a resting position or a sleeping position (e.g., lying down, etc.). The sleep surface 15 may include a head portion 16 adjacent to the head end 13 of the mattress 10, a foot portion 18 adjacent to the foot end 14 of the mattress 10, and an intermediate portion 17 between the head portion 16 and the foot portion 18. The head portion 16 may receive a head, neck, and shoulders of an individual and, optionally, an upper part of the individual's chest, or thorax. The intermediate portion 17 may receive the individual's chest, abdomen, and hips and, optionally, upper parts of the individual's legs. The foot portion 18 may receive the individual's lower legs and feet.

The cushioning element 20 of the mattress 10 may comprise any suitable type of cushioning element, such as conventional springs and foam, foam, memory foam, pressurizable bladders (e.g., air chambers, etc.), a gel grid with a plurality of interconnected walls that define hollow columns (e.g., the gel grids of the mattresses available from Purple Innovation, LLC, of Lehi, Utah and disclosed by U.S. Pat. Nos. 7,060,213, 7,076,822, and 8,919,750, which may be formed from any suitable material, including, but not limited to, an extended A-B-A triblock copolymer, such as those disclosed by U.S. Pat. Nos. 6,413,458, 6,797,765 and 7,964,664; the entire disclosures of each of the foregoing patents are hereby incorporated herein), or any combination of these and/or other features. Some nonlimiting examples of mattresses cushioning element 20 arrangements that may be employed in a mattress 10 of this disclosure are described by U.S. Pat. Nos. 11,317,733 and 11,213,139, the entire disclosures of which are hereby incorporated herein.

The rails 30 of the mattress 10 may include side rails 30s positioned laterally adjacent to sides of the cushioning element 20. The side rails 30s may at least partially define the sides 12 of the mattress 10. In some embodiments, the rails 30 may also include a head rail 30h adjacent to a head end of the cushioning element 20 and/or a foot rail 30f adjacent to a foot end of the cushioning element 20. A head rail 30h may at least partially define the head end 13 of the mattress 10. A foot rail 30f may at least partially define a foot end 14 of the mattress 14. In embodiments where a mattress 10 includes side rails 30s, a head rail 30h, and a foot rail 30f, the rails 30 may laterally surround the cushioning element 20.

Each rail 30 may comprise any suitable material. As an example, each rail 30 may comprise a structured foam. As another example, side rails 30s that at least partially define sides 12 of the mattress 10 may include bodies 32 formed from a somewhat rigid material with cutouts 34 at locations to accommodate bending the mattress 10, as would be expected to occur when the mattress 10 is used with an adjustable platform. The cutouts 34 may be filled with inserts 36 comprising a material that is softer and more readily compressible than the material from which the bodies 32 of the side rails 30 are formed. In such embodiments, the bodies 32 of the side rails 30s may be formed from a structured foam, while inserts 36 formed from a softer foam may fill the cutouts 34 in the side rails 30s. Examples of such side rails 30s are described by U.S. Patent Application Publication US 2022/0287469 A1, the entire disclosure of which is incorporated herein.

Each sensor 40 may be carried by the mattress 10. Without limitation, at least one sensor 40 may be positioned adjacent to the sleep surface 15 of the mattress 10. For example, a sensor 40 may be positioned within a cover 11 of the mattress 10 in a manner that enables the sensor 40 to detect activity occurring on a sleep surface 15 of the mattress 10. More specifically, as seen in FIG. 3, each sensor 40 may be positioned within a recess or a receptacle 44, 46 that opens to and communicates with an outer surface of a component (e.g., the cushioning element 20, a rail 30, etc.) of the mattress 10 that carries the sensor 40, with the cover 11 being placed over the recess or receptacle 44. In other embodiments, the sensor 40 may be incorporated into the cover 11 or positioned between the cover 11 and internal components (not shown) (e.g., a top layer of foam, gel, etc.) of the mattress 10.

In some embodiments, the mattress 10 may carry a plurality of sensors 40. Without limitation, at least one thoracic sensor 40T may be positioned at the head portion 16 and/or the intermediate portion 17 of the sleep surface 15 of the mattress 10. At least one leg sensor 40L may be positioned at the foot portion 18 of the sleep surface 15. At least one edge sensor 40E may be positioned at a side 12 or end 13, 14 (e.g., on, adjacent to, or within a rail 30, etc.) of the mattress 10. In a specific embodiment, the mattress 10 may comprise a gel grid 42. Each thoracic sensor 40T and/or leg sensor 40L may be positioned within a hollow column 44 defined by interconnected walls 43 of the gel grid 42. The hollow column 44 may comprise a recess or receptacle adjacent to an upper surface 45 of the gel grid 42. Each edge sensor 40E may be positioned within a recess or receptacle 46 that opens to or otherwise communicates with an outer surface 31 of a side rail 30s of the mattress 10.

In the illustrated embodiment of the mattress 10, which has a size that accommodates two individuals, each thoracic sensor 40T and leg sensor 40L is shown at a location where an individual is expected to lie on the sleep surface 15 of the mattress 10 as he or she sleeps. Thus, the mattress 10 may include two thoracic sensors 40T, two foot sensors 40F, and two edge sensors 40E. Each thoracic sensor 40T is located at a transition between the head portion 16 of the sleep surface 15 and an upper extent of the intermediate portion 17 of the sleep surface 15. Each foot sensor 40F is located at the foot portion 18 of the sleep surface 15. Each edge sensor 40E is located in a side rail 30 at a location adjacent to a transition between the lower extent of the intermediate portion 17 of the sleep surface 15 and the foot portion 18 of the sleep surface 15.

In other embodiments, including small mattresses (e.g., twin size, twin XL (extra long) size, full size, etc.) and large mattresses (e.g., queen size, king sizes, etc.), thoracic sensors 40T and leg sensors 40L may be positioned along a midline of the mattress—alone or in combination with other sensor placements. Of course, a mattress 10 of this disclosure may include any other arrangement of sensors 40.

Each sensor 40 may be a single type of sensor or include a variety of types of sensors. Without limitation, each sensor 40 may comprise one or more of in inclinometer, an accelerometer, a temperature/humidity sensor, a proximity sensor, an ambient light sensor, a pressure sensor, or the like.

The at least one thoracic sensor 40T may facilitate detection of the presence (or absence) of an individual on the sleep surface 15 of the mattress 10. In addition, the at least one thoracic sensor 40T may be used to monitor one or more of the individual's movement (e.g., motion, position on the sleep surface 15, etc.), respiration, and heart rate. The at least one thoracic sensor 40T may also monitor the temperature of the individual's body and, optionally, humidity. In a specific embodiment, the at least one thoracic sensor 40T may include an inclinometer (e.g., an inclinometer available from STMicroelectronics of Plan-les-Ouates, Switzerland, etc.), an accelerometer (e.g., an accelerometer available from MEMSIC Inc. of Andover, Massachusetts, etc.), and a plurality of temperature/humidity sensors (e.g., a temperature and/or humidity sensor available from Sensiron AG of Stäfa, Switzerland, etc.).

The at least one leg sensor 40L may facilitate the detection of the presence (or absence) of an individual on the sleep surface 15 of the mattress 10. In addition, the at least one leg sensor 40L may be used to monitor the individual's movement (e.g., motion, position, etc.), respiration, and heart rate. The at least one leg sensor 40L may monitor the temperature of the individual's legs and, optionally, humidity. In a specific embodiment, the at least one leg sensor 40L may include an accelerometer (e.g., an accelerometer available from MEMSIC Inc. of Andover, Massachusetts, etc.) and a plurality of temperature/humidity sensors (e.g., a temperature and/or humidity sensor available from Sensiron AG of Stäfa, Switzerland, etc.).

The at least one edge sensor 40E may facilitate the detection of the presence (or absence) of an individual in proximity to a side 12 or an end 13, 14 of the mattress 10 or on the sleep surface 15 of the mattress 10. In addition, the at least one edge 40E may be used to monitor information about an environment (e.g., a room, etc.) within which the mattress 10 is located, such as its temperature and/or humidity. In a specific embodiment, the at least edge sensor 40E may include an accelerometer (e.g., an accelerometer available from MEMSIC Inc. of Andover, Massachusetts, etc.) and a temperature/humidity sensor (e.g., a temperature and/or humidity sensor available from Sensiron AG of Stäfa, Switzerland, etc.).

The processor 50 may comprise one or more processing elements of a suitable type (e.g., microprocessors, microcontrollers, digital signal processors (DSPs), etc.). In some embodiments, the processor 50 may comprise one or more microcontrollers, which may execute embedded programming (e.g., firmware) to control one or more dedicated functions. The processor 50 may be carried by the mattress 10 (e.g., internally, adjacent to a foot end 14 of the mattress 10 (e.g., by a foot rail 30*f*, etc.).

Activity detected by the sensor(s) 40 may be communicated to the processor 50 (e.g. by wires, wirelessly, etc.). The processor 50 may execute a program to process the data from the sensor(s) 40, which may indicate that an individual has approached the mattress 10, indicate that an individual has assumed a resting position or a sleeping position on the sleep surface 15 of the mattress 10, indicate movement by the individual on the sleep surface 15, provide information about an individual on the sleep surface 15 (e.g., the individual's respiratory rate, whether the individual is snoring, the individual's heart rate, a temperature of a body part of the individual, a relative humidity generated by part of the individual's body, etc.), provide information about a state of the mattress 10 (e.g., whether pillows or bedding have been moved over the sleep surface 15, etc.), provide information about the environment in which the mattress is located (e.g., temperature, humidity, light intensity, etc.), or the like.

In response to information obtained by processing data from the sensor(s) 40, the processor 50 may execute one or more programs that affect a state of the mattress 10, a bed of which the mattress 10 is a part, and/or the environment in which the mattress 10 is located.

The transceiver 52 of the mattress 10 may be associated with the processor 50 in a manner that enables the processor 50 to communicate with a processor of another device. Without limitation, the transceiver 52 may facilitate communication between the processor 50 and a processor of an adjustable foundation that carries the mattress 10, a processor of a remote control used with the mattress 10, a processor of a portable electronic device (e.g., a smart phone, a tablet computer, a smart watch, etc.) used by an individual who sleeps on or otherwise controls use of the mattress 10, or a processor of another device that may be used in conjunction with the mattress 10. Without limitation, the transceiver 52 may comprise one or more of a WiFi transceiver, a 2.4 GHz radiofrequency (RF) transceiver, a Bluetooth® transceiver, a near-field communication (NFC) (e.g., radiofrequency, etc.) transceiver, or the like, along with its associated antenna. The transceiver 52 may be carried by the mattress 10 or elsewhere. In some embodiments, the transceiver 52 may be associated with (e.g., located adjacent to, packaged with, etc.) the processor 50 of the mattress 10.

Other optional components of the mattress 10 include, without limitation, one or more pressurizable bladders and an associated pressurization system (see, e.g., U.S. Pat. No. 11,213,139 and U.S. Patent Application Publication US 2022/0273113 A1, the entire disclosures of which are hereby incorporated herein), a ventilation system and/or temperature control system (see, e.g., U.S. Pat. No. 11,311,111, the entire disclosure of which is hereby incorporated herein), a remote control, and the like. Additionally, the mattress 10 may be part of a bed, or even part of a smart bed, which may also include and function in conjunction with an adjustable foundation (e.g., the Purple® Ascent Base™ adjustable platform, available from Purple Innovation, LLC, of Lehi, Utah, etc.).

Although this disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

What is claimed:

1. A mattress, comprising:
   a cushioning element including:
      an upper surface with a head portion, an intermediate portion, and a foot portion, and
      an outer periphery including ends and sides of the cushioning element;
   rails adjacent to the sides of the cushioning element;
   at least one thoracic sensor positioned adjacent to the upper surface of the head portion of the cushioning element or adjacent to the upper surface of the intermediate portion of the cushioning element;
   at least one leg sensor positioned adjacent to the upper surface in the foot portion of the cushioning element; and
   at least one edge sensor positioned within a receptacle of a rail of the rails, the receptacle positioned between the head portion and the foot portion of the cushioning element, and the receptacle positioned to open towards an outer top surface of the rail.

2. The mattress of claim 1, wherein the at least one thoracic sensor monitors respiration, heart rate, and movement.

3. The mattress of claim 2, wherein the at least one thoracic sensor further monitors temperature and humidity.

4. The mattress of claim 3, wherein the at least one thoracic sensor comprises an inclinometer, an accelerometer, and a plurality of temperature/humidity sensors.

5. The mattress of claim 1, wherein the at least one leg sensor monitors movement.

6. The mattress of claim 5, wherein the at least one leg sensor further monitors temperature and humidity.

7. The mattress of claim 6, wherein the at least one leg sensor comprises an accelerometer and a plurality of temperature/humidity sensors.

8. The mattress of claim 1, wherein the at least one edge sensor monitors an environment in which the mattress is located.

9. The mattress of claim 1, wherein the at least one edge sensor monitors movement.

10. The mattress of claim 9, wherein the at least one edge sensor monitors movement and a room in which the mattress is located.

11. The mattress of claim 9, wherein the at least one edge sensor further monitors temperature and humidity.

12. The mattress of claim 9, wherein the at least one edge sensor comprises an accelerometer and a temperature/humidity sensor.

13. A mattress, comprising:
   a cushioning element including:
      an upper surface with a head portion, an intermediate portion, and a foot portion, and
      an outer periphery including ends and sides of the cushioning element;
   rails adjacent to the sides of the cushioning element;
   at least one thoracic sensor that monitors movement, temperature, and humidity positioned adjacent to the upper surface of the head portion of the cushioning element or adjacent to the upper surface of the intermediate portion of the cushioning element;
   at least one leg sensor that monitors movement positioned adjacent to the upper surface in the foot portion of the cushioning element; and
   at least one edge sensor positioned within a receptacle of a rail of the rails, the receptacle positioned between the head portion and the foot portion of the cushioning element, and the receptacle positioned to open towards an outer top surface of the rail.

14. A method for monitoring use of a mattress, comprising:
   monitoring metrics of an individual on the mattress including:
      monitoring movement of the individual, a respiratory rate of the individual, and a heart rate of the individual at or adjacent to a head portion of the mattress;
      monitoring movement of the individual at or adjacent to a foot portion of the mattress;
      monitoring a presence of the individual in proximity to at least one side of the mattress via at least one edge sensor positioned within a side of the at least one side, the at least one edge sensor positioned in a receptacle of the side that is positioned to open towards an outer top surface of the side; and
      monitoring an ambient environment at a periphery of the mattress; and
   providing at least one metric regarding the individual on the mattress to a portable device.

15. The method of claim 14, further comprising:
   monitoring temperature and humidity at or adjacent to the head portion of the mattress and at or adjacent to the foot portion of the mattress.

16. The method of claim 14, wherein monitoring the ambient environment comprises monitoring a temperature and a humidity of the ambient environment.

17. The method of claim 14, further comprising:
   detecting at least one of placement of the individual on the mattress and removal of the individual from the mattress.

18. The method of claim 14, further comprising:
   adjusting the mattress in response to data obtained from any of the foregoing acts of monitoring.

19. The method of claim 18, wherein adjusting the mattress comprises adjusting an orientation of one or more portions of the mattress, adjusting ventilation of the mattress, and/or adjusting a temperature of the mattress.

* * * * *